(12) United States Patent
Niemetz et al.

(10) Patent No.: US 11,191,882 B2
(45) Date of Patent: Dec. 7, 2021

(54) APPARATUS FOR EXTRACORPOREAL BLOOD TREATMENT WITH AUTOMATIC MONITORING OF RESPIRATORY RATE

(71) Applicant: B. BRAUN AVITUM AG, Melsungen (DE)

(72) Inventors: Günter Niemetz, Melsungen (DE); Ralf Niebeling, Melsungen (DE)

(73) Assignee: B. BRAUN AVITUM AG, Melsungen (DE)

(*) Notice: Subject to any disclaimer, the term of this patent is extended or adjusted under 35 U.S.C. 154(b) by 982 days.

(21) Appl. No.: 15/886,380

(22) Filed: Feb. 1, 2018

(65) Prior Publication Data

US 2018/0221560 A1 Aug. 9, 2018

(30) Foreign Application Priority Data

Feb. 3, 2017 (DE) .................. 10 2017 102 169.8

(51) Int. Cl.
| | | |
|---|---|---|
| *A61M 1/36* | (2006.01) | |
| *A61M 60/50* | (2021.01) | |
| *A61M 60/113* | (2021.01) | |
| *A61M 60/279* | (2021.01) | |

(52) U.S. Cl.
CPC ........ *A61M 1/3656* (2014.02); *A61M 1/3639* (2013.01); *A61M 1/3659* (2014.02); *A61M 60/113* (2021.01); *A61M 60/279* (2021.01); *A61M 60/50* (2021.01); *A61M 2205/13* (2013.01); *A61M 2205/15* (2013.01); *A61M 2205/18* (2013.01); *A61M 2205/3331* (2013.01); *A61M 2230/40* (2013.01); *A61M 2230/42* (2013.01)

(58) Field of Classification Search
CPC .............. A61M 1/3656; A61M 1/3659; A61M 1/3639; A61M 60/279; A61M 60/113; A61M 2205/13; A61M 2205/15; A61M 2205/18; A61M 2205/3331; A61M 2230/40; A61M 2230/42
See application file for complete search history.

(56) References Cited

U.S. PATENT DOCUMENTS

| | | | |
|---|---|---|---|
| 3,483,880 A | 12/1969 | Namerow | |
| 4,958,638 A * | 9/1990 | Sharpe | ................ A61B 5/0205 |
| | | | 600/407 |
| 6,595,942 B2 | 7/2003 | Kleinekofort | |
| 8,529,485 B2 | 9/2013 | Bock et al. | |

(Continued)

FOREIGN PATENT DOCUMENTS

| | | |
|---|---|---|
| DE | 19848235 C1 | 3/2000 |
| DE | 102006060819 A1 | 7/2003 |

(Continued)

OTHER PUBLICATIONS

Brendebach Luca Notarzt, Schockforum (Types of Shock), 2013 with English translation—14 pages.

(Continued)

*Primary Examiner* — Philip R Wiest

(57) ABSTRACT

An apparatus and method for extracorporeal blood treatment, especially a dialysis apparatus, are disclosed, the apparatus includes a radar sensor for monitoring a patient located at a place of treatment.

10 Claims, 2 Drawing Sheets

(56) References Cited

U.S. PATENT DOCUMENTS

| | | | |
|---|---|---|---|
| 8,632,486 B2 * | 1/2014 | Muller | A61M 1/3661 604/6.04 |
| 2007/0118954 A1 | 5/2007 | Pinhas et al. | |
| 2008/0269589 A1 * | 10/2008 | Thijs | A61B 5/05 600/407 |
| 2010/0004552 A1 | 1/2010 | Zhang et al. | |
| 2011/0046534 A1 | 2/2011 | Gross | |
| 2014/0102957 A1 * | 4/2014 | Broeker | G01G 19/445 210/85 |
| 2015/0253860 A1 | 9/2015 | Merics et al. | |
| 2015/0359955 A1 | 12/2015 | Wolff et al. | |

FOREIGN PATENT DOCUMENTS

| | | |
|---|---|---|
| DE | 102008013090 A1 | 9/2009 |
| DE | 102014108227 A1 | 12/2015 |
| EP | 1574178 A2 | 9/2005 |
| EP | 1892001 A1 | 2/2008 |
| EP | 2857053 A1 | 4/2015 |
| WO | 9924145 A1 | 5/1999 |
| WO | 0147581 A1 | 7/2001 |
| WO | 03086506 A1 | 10/2003 |

OTHER PUBLICATIONS

German Search Report for Application No. 10 2017 102 169.8, with partial translation, dated Aug. 14, 2017—13 pages.

* cited by examiner

APPARATUS FOR EXTRACORPOREAL BLOOD TREATMENT WITH AUTOMATIC MONITORING OF RESPIRATORY RATE

CROSS REFERENCE TO RELATED APPLICATIONS

This application claims priority to German application DE 10 2017 102 169.8 filed Feb. 3, 2017, the contents of such application being incorporated by reference herein.

FIELD OF THE INVENTION

The invention relates to an apparatus for extracorporeal blood treatment comprising a system for detecting needle disconnection. In particular, the invention relates to a medical device in which blood loss may occur to the patient due to leakages in the extracorporeal circuit or defects at a patient's access.

BACKGROUND OF THE INVENTION

Medical devices for extracorporeal blood treatment usually include a blood treatment apparatus, such as in the form of a dialyzer, which is connectable to a patient's blood circulation via extracorporeal lines. Moreover, those devices comprise a blood pump, a control unit for controlling the blood pump and for monitoring operating states. A typical treatment carried out by said devices is the dialysis treatment that is usually carried out in specific buildings. As a rule, 20 to 50 treatment places distributed to several rooms are provided. Nursing staff is in charge of monitoring the patients during treatment. However, it is a drawback that it is not possible to ensure constant presence of a nursing staff member near a patient for monitoring, as one nursing staff member usually has to care for several patients. Therefore, efforts have been made to shift monitoring of the patient at least in part to the medical device and thereby detecting risks for the patient, performing appropriate safety control and calling for the nursing staff to attend to the patient. However, when extracorporeal blood loss occurs as a result of disconnection in the venous return, at present the safety of the patient is ensured only by careful monitoring by the nursing staff, as commonly employed venous pressure monitoring as a protective system is not capable of safely detecting a blood loss in each case.

During extracorporeal blood treatment, such as hemodialysis or plasm therapy, a patient's blood flows from an arterial vascular access via a filter to a venous vascular access. Frequently, the access to the vascular system is an arterio-venous fistula applied by surgery which is generally punctured by an arterial and venous cannula (double needle). Equally, the use of a vascular implant (shunt) is possible. A vascular access is understood to be any type of access to a patient's vascular system, but in particular a connection between a patient's artery and vein. As yet, there has been no safe device for avoiding blood loss especially in double-needle treatment. In order to prevent the needle from disconnecting, at present the lines leading to or from a vascular access are bonded with the aid of plasters. Further, conventional dialysis devices are measuring the flow resistance between the apparatus and the patient when the blood is returned to the patient. Thereby, blood is conveyed through the cannula into the patient at a flow rate of from 200 to 600 ml/min. Merely the flow resistance of the cannula is mostly located within the pressure monitoring range of the dialysis device. When the venous cannula disconnects, blood flows from the arterial vascular access via the dialysis device out of the patient. The dialysis device reacts due to secondary effects such as the pressure drop at the venous pressure sensor. However, the pressure drop is dependent on blood flow, hematocrit, cannula and vascular pressure of the patient. In the normal case, the nursing staff adjusts a lower limit to be as close to the current venous pressure as possible, however without knowing the exact pressure that likely appears when the cannula has disconnected. On principle, there are two options, namely either the dialysis device will give an alarm without the cannula having disconnected and thus will call for the nursing staff to see to the device or the dialysis device will not give an alarm when the cannula has disconnected and the patient will lose blood.

DESCRIPTION OF THE RELATED ART

From the state of the art approaches for controlling the machine during extracorporeal blood treatment are known. For example, the patent application US 2015 0253860 A1 describes a control of a dialysis machine using an electric field, wherein the machine may be controlled with a user's gestures. Similarly, EP 2 857 053 describes a detection of gestures within a detection range of a movement detection unit so as to control a dialysis device, for example with the aid of a camera and a camera-less sensor. DE 10 2006 060 819 A1 describes a dialysis machine in which information about the respiratory frequency is further used for the dialysis treatment.

Moreover, numerous different methods and apparatuses for general monitoring of vital parameters of patients are known. For example, US 2007 0118054 A1 discloses a method and a system for monitoring vital parameters, wherein for example the respiration is recorded for detecting various respiratory patterns. A sensor is placed beneath the patient and then is capable of detecting corresponding patterns. Said patterns serve for monitoring vital functions for predicting and treating physiological disease such as e.g. asthma, hypoglycemia, coughing, edema, sleep apnea, labor and REM sleep stages. US 2008 0269589 A1 describes a portable radar sensor that introduces a radar signal into the thorax and receives the reflected signal again. The device serves for measuring and monitoring the mechanical heart activity. U.S. Pat. No. 4,958,638 describes a radar technology adapted to measure a patient's heart rate and respiration rate within a reach of approx. 6 meters. The non-contact vital signal monitor is employed to assist therapies in hospitals as well as in nursing homes. U.S. Pat. No. 3,483,860 describes detection of a patient's respiratory frequencies without any radar technology, wherein a transmission sensor is placed above the patient and a receiver sensor is placed beneath the patient.

Moreover, approaches for monitoring a patient during extracorporeal blood treatment are known. A general approach is disclosed in EP 1 574 178 A1, namely in the form of a medical therapeutic system in which a video camera is directed to a treatment station. The picture of the video camera is reproduced on the screen of a remote physician's desk. In this way, the physician can visualize and monitor the patient. It is a drawback that continuous monitoring is not possible and only few patients can be simultaneously monitored. Another use of a camera is described in EP 1 892 001 A1, wherein a camera is directed to a dialysis therapy station. The picture of the camera is processed in a computing unit incorporated in the dialysis machine such that the color of the blood and/or the arrangement thereof in the image surface is established in the camera picture, with the size of the recorded image surface being further evaluated by the color of the blood. In this way, extracorporeal blood loss can be automatically detected, signaled and the blood pump can be stopped. However, it is a drawback that cameras without any additional measures (such as an infrared recognition) are functional at daytime only, i.e. by daylight, and that the camera pictures taken provide pictures related to persons so that protection of anonymity can be achieved by additional measures only.

For example WO 99/24145 A1 is known as prior art for detecting blood loss during extracorporeal blood treatment, which describes a pair of electrodes being arranged, during dialysis, in the vicinity of a cannula and being connected to the dialysis device by two lines. When the needle disconnects from the patient, the outflowing blood establishes a conductive connection between the electrodes. This is detected by the dialysis device. The controller of the dialysis device stops the blood flow and alarms the staff. It is detrimental that the method requires additional manipulations that have to be carefully carried out by the staff members. In addition, false alarms may be triggered when other liquids, such as sweat, are depositing between the electrodes. Similarly, WO 01/47581 A1 discloses an array of electrodes for extracorporeal blood treatment. The electrodes serve for detecting loss of blood by current capacitively coupled between the arterial branch and the venous branch by a generator. A voltage drop caused by current flow in the blood within the line is judged. If either of the cannulas disconnects, the current is reduced which is detected. It is a drawback in this method that a needle which is not completely disconnected is not detected. DE 198 48 235 C1 discloses a system judging the arterial pressure and the venous pressure so as to detect disconnection of the venous cannula therefrom. It is a drawback in this method that the dynamic behavior of the extracorporeal circulation is also judged which may result in false judgments. Moreover, the method does not solve the problem of indirect measurement of the blood loss, as the extracorporeal pressure is no measure of the loss of blood. WO 03/86506 A1 describes an electric contact that is directly introduced to the blood. It is detected with constant current and judgment of voltage drop whether the cannula has disconnected. In this case, it is a drawback that a cannula which has not completely disconnected is not detected and, in addition, the tubing system is cost-intensive, because the electric contacts need to be introduced.

SUMMARY OF THE INVENTION

Based on the afore-described state of the art, an object underlying the present invention is to eliminate the afore-listed drawbacks, in particular to configure a medical device including an extracorporeal blood circuit so that excessive blood loss of a patient during treatment will be safely detected.

According to aspects of the invention, this object is achieved, in accordance with the independent claims, by an apparatus for extracorporeal blood treatment, especially by a dialysis apparatus, comprising a radar sensor for monitoring a patient located on a place of treatment. According to aspects of the invention, the apparatus forms, along with an evaluation unit for signals of the radar sensor, a system for detecting the respiratory frequency and/or respiratory amplitude of a patient. The evaluation unit may be configured separately from the apparatus for extracorporeal blood treatment or integrally with the latter. The radar sensor is directed or can be directed to the place of treatment and, respectively, to the patient located there. In accordance with the invention, the radar sensor transmits signals and receives the signals reflected by the patient. The information about the patient's condition contained in the received signals are evaluated by the evaluation unit.

According to aspects of the invention the evaluation unit to which the radar sensor supplies its information may perform especially one or more of the following cycles:

Localizing and/or detecting one or more patients, wherein especially movements of the patient's thorax can be detected and/or recognized and/or monitored.

Converting a detected thorax movement to respiratory frequency and/or amplitude.

Comparing the detected respiratory frequency values and/or amplitude values to at least one limit value, where appropriate to a limit value defined before.

Stopping the blood pump and closing at least one tube shutoff clamp upon exceeding and/or falling below the limit value.

Triggering an alarm when/if the limit value is not observed, for example in the case of deviation from a value of 12 to 18 respirations/minute and/or more than 20 respirations/minute (tachypnea) and/or less than 10 respirations/minute (bradypnea).

Summing up, it can be stated that, according to aspects of the invention, the evaluation unit may be especially arranged and configured to compare the detected respiratory frequency values and/or amplitude values to limit values and to take the steps derived therefrom, i.e. stopping the blood pump and closing the tube shutoff clamp, when/if the limit value is exceeded and/or fallen below, and/or giving the alarm.

Advantages achieved by the invention with respect to known solutions of the state of the art for detecting venous needle disconnection especially reside in non-contact monitoring of respiration to detect the patient's general state of health or as feedback for problems during dialysis treatment, wherein in the case of dialysis at night efficient monitoring of the patient's state of health is possible and wherein monitoring can be carried out basically anonymized. Furthermore, additional vital parameters such as faint can be detected in a contactless manner by hypotensive episodes.

Advantageous embodiments of the invention are claimed in the dependent claims and shall be illustrated in detail below.

A preferred embodiment of the invention provides the radar sensor to be directly integrated in the apparatus. This offers the advantage that the apparatus can be used as a mobile unit and connection of the radar sensor to the apparatus and the control thereof are especially easy to implement. The radar sensor may be integrated in the apparatus especially by common means such as an infusion rod attached to the apparatus or the like. Preferably, the radar sensor is arranged to be capable of being positioned on the apparatus.

Preferably, the apparatus includes a reference mark adapted to be attached to the patient, especially to his/her thorax. Said reference mark interacts with the radar sensor in a sensory manner, i.e. the radar sensor can detect both the reference mark as such and the position and/or change of position thereof relative to the sensor. As a result of coupling the reference mark to the patient, safe detection of movements of the patient or particular body areas (thorax) relative to the sensor can be facilitated so that the respiratory frequency of the patient can be recorded easily and conveniently for the patient. The reference mark may be a tag or button, for example, and may be fastened to a target area, for example to the patient's thorax. If the reference mark is not found, an alarm may be given according to a further embodiment of the invention.

In accordance with a preferred embodiment, the apparatus comprises at least one shutoff member for shutting off a line connected to the patient at the venous branch. Alternatively or additionally, the apparatus comprises at least one shutoff member for shutting off a line connected to the patient at the arterial branch. The respective shutoff member may be especially in the form of a tube clamp pinching off an elastic or flexible area of a blood line of the apparatus or of an extracorporeal tube system. In the case of needle disconnection, quick disconnection/shut-off of the line system from the patient can be ensured in this way so that the patient's loss of blood can be minimized.

Moreover, the apparatus may include a control unit which is arranged and configured so as to establish a respiratory frequency of the patient by way of signals of the radar sensor. The patient's respiratory frequency can be monitored automatically and continuously without great effort in this way, thus enabling an especially high safety standard. In particular, the control unit may be arranged and configured so as to trigger an alarm signal, if the respiratory frequency detected by the radar sensor deviates from a preset limit value or from plural preset limit values (increases and/or decreases). For example, alarm can be triggered if/when an increased respiratory frequency (e.g. of more than 20 respirations/min) is detected for a defined period of time (e.g. 30 sec). The shutoff member may be automatically operable via the control unit in the event of alarm.

In a preferred embodiment of the invention, a blood detector may be provided in the extracorporeal line system, which blood detector permits the activation of radar monitoring only if/when blood is detected. For instance, said blood detector is a red detector, which detects red liquid in the line system of the apparatus or in the tube system. This embodiment provided the advantage that radar monitoring is carried out only when the patient is connected to the extracorporeal tube system and the blood flows into the latter.

According to a preferred embodiment of the invention the radar sensor can be positioned/aligned, preferably automatically positioned, with a drive for readjusting, especially automatically readjusting, the alignment of the radar sensor relative to the patient. This permits an uncomplicated adjustment of the apparatus which is especially convenient for the patient. Furthermore, with the drive the radar sensor may be ensured to record the correct target area. The drive may be especially part of the radar sensor or of the apparatus.

According to a further embodiment of the invention, transmission of information from the radar sensor to the evaluation unit may be carried out via cables or via a wireless connection, e.g. WLAN, Bluetooth or the like. Moreover, it is possible to provide plural radar sensors which are monitoring the target area from different directions.

According to an embodiment of the invention, the apparatus may include a reading device arranged and suited for detecting an identification of an operator, for instance a machine-readable staff ID card. The data of said identification are stored so that it is documented which person has manipulated the apparatus at which time and which settings have been taken. Reading in the identification may inform about a nursing staff member being present at the place of treatment. This may be considered for evaluating the signals indicating the patient's state of health. For example, the previous respiratory frequency may be considered as reference variable so that only changes that have occurred since the appearance of the nursing staff member are recorded.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
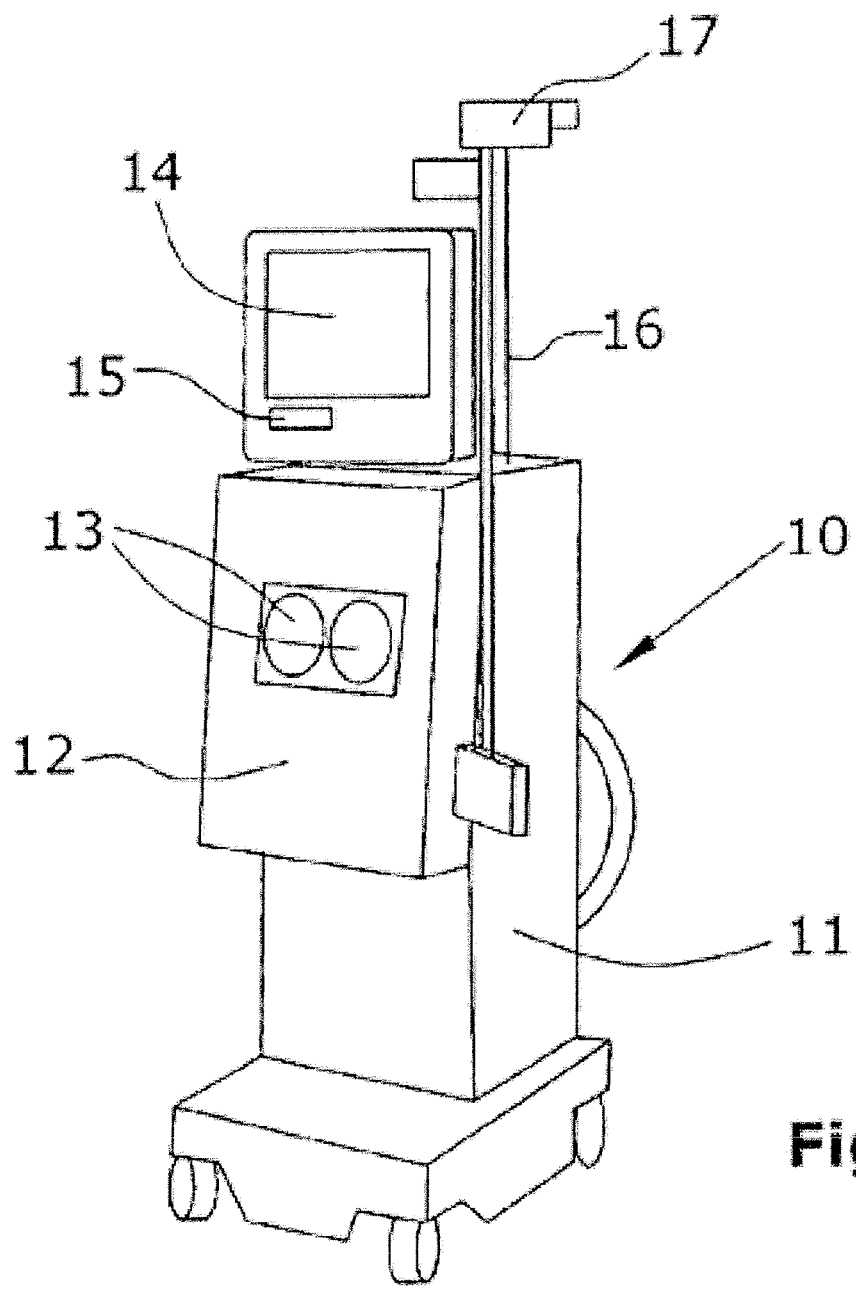
FIG. 1 shows a perspective view of the apparatus in the form of a device for hemodialysis, hemofiltration or plasma treatment

FIG. 1 illustrates an embodiment of the apparatus 10 according to aspects of the invention in the form of a medical device 10 for extracorporeal blood treatment. It includes a device base 11 in which mechanical components such as e.g. lines, valves etc. not shown in the Figure are located. At its front side the base 11 supports a console 12 in which two blood pumps 13 accessible from outside are arranged. The blood pumps 13 are peristaltic pumps the tubes of which (not shown in the Figure) are inserted from the front side in a generally known manner.

On the device base 11 a control unit 14 constituting an interface for communication with a user is located. The control unit 14 in this case includes a touchscreen monitor via which the user may retrieve various menus and may query operating states as well as enter data and instructions. A card reader 15 into which the user may insert a machine-readable ID card is provided.

A radar sensor 17 is attached to a rod or infusion rod 16 preferably mounted on the device base/housing 11. Radar pictures recorded by the radar sensor 17 are wirelessly transmitted to the control unit 14 in the present embodiment. The radar sensor 17 is directed to a patient's place not shown but located in the vicinity of the apparatus 10, e.g. a couch on which the patient is lying during blood treatment. In this way, the patient is detected by the radar sensor 17. In this context, it is noted that the radar sensor 17 may also be mounted directly on the device base/housing 11.

The patient is connected to the device 10 in a known way via tubes (not shown) of an extracorporeal blood tube system.

Figure 2:
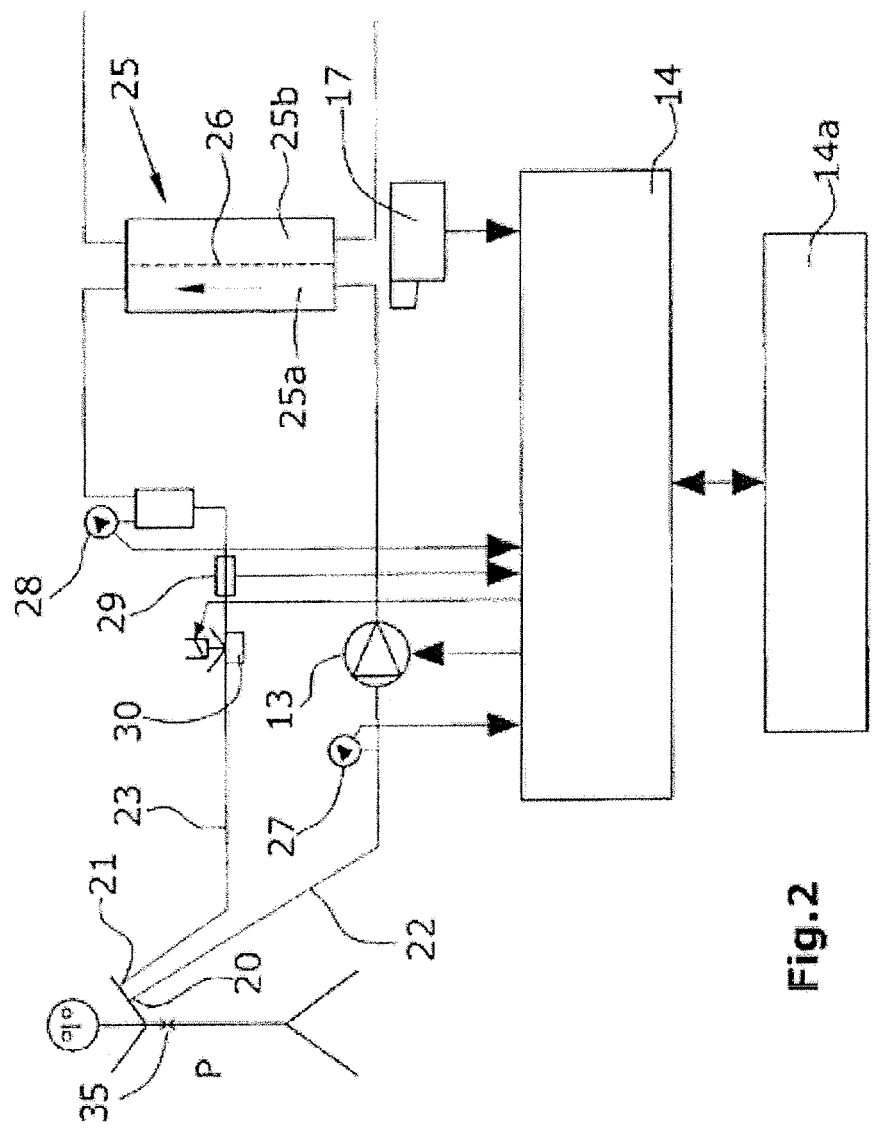
FIG. 2 shows a schematic representation of the substantial functional parts of the dialysis device.

In FIG. 2 a patient P is schematically represented. One arm of the patient P is provided with an arterial access 20 and a venous access 21. An arterial tube line 22 leads from the arterial access 20 to the blood pump 13. The latter pumps blood through a blood chamber 25a of a therapeutic device 25 in the form of a dialyzer 25; the two chambers 25a, 25b of which are separated by a membrane 26. The chamber 25b is a dialysate chamber through which dialysate flows.

After leaving the chamber 25a the blood continues to flow into a venous tube line 23 connected to the venous vascular port 21 or access 21. In this way, a blood circulation is formed.

Where appropriate, a pressure gauge 27 measures the arterial blood pressure in the arterial line 22. In the same way, a pressure gauge 28 measures the venous blood pressure in the venous line 23, where appropriate. Furthermore, the venous line 23 interacts indirectly or directly with a red detector 29, where necessary, which detects the presence of blood in the tube line and reports it to the control unit 14. For example, the venous line 23 comprises the detector 29. The pressure gauges 27, 28 as well as the detector 29 (if present) are connected to the control unit 14 for the purpose of control. The control unit controls the entire operation of the device 10 and monitors the described functions as well as a number of further functions not explained in detail here.

In order to be able to shut off the blood circulation, preferably a tube shutoff clamp 30 controlled by the control unit 14 is provided in the venous line 23. In the arterial line 22, too, a shutoff member may be provided preferably in the form of the blood pump 13. The blood pump 13 is a peristaltic pump which is continuously pinched by a pinching member. In the case of standstill of the blood pump 13, the latter acts as a shutoff member which closes the tube line.

The radar sensor 17 and its connection to the control unit 14 are evident from FIG. 2.

A reference mark 35 which can be detected by the radar sensor 17 is preferably arranged on the body of the patient P, in this case on his/her thorax. The radar sensor 17 is adjusted, possibly automatically adjusted, by a motion drive (not shown) so that the reference mark 35 is located at a particular position in the radar picture. This helps to ensure that, irrespective of movements of the patient P, the radar sensor 17 is always directed to the desired target area.

The control unit 14 in FIG. 2 is a computer comprising a memory unit. The latter performs all monitoring and control cycles as well as generations of alarm. The control unit 14 is connected to a display, operating and communication unit 14a.

During dialysis, an extracorporeal blood flow of from 50 to 600 ml/min is taken from the patient P by the blood pump by withdrawing blood with the peristaltic pump 13 from the arterial cannula 20 and the subsequent line 22 and by returning blood via the venous cannula 21 and the subsequent line 23. The blood is guided in the lines 22, 23 to which components such as the cannulas 20, 21, the pressure sensors 27, 29 and the dialyzer 25 are connected. Control and monitoring are implemented with the control, computing and memory unit 14. The parameters for the patient P to be treated are entered via the display, operating and communication unit 14a. For interrupting the blood flow, the control unit 14 stops the blood pump 13 and closes the tube shutoff clamp 30. Moreover, an optical and acoustic alarm is triggered. This protects the patient P from further damage as no further blood loss may occur.

During therapy, the control/analysis unit 14 continuously compares the current respiratory frequency (about 12-18 respirations/min) to set upper and/or lower limit values. For this purpose, the at least one radar sensor 17 detects the movements of the reference mark 35 and transmits corresponding signals to the control unit 14. The control unit establishes respirations from the received signals and herefrom calculates the respiratory frequency and/or the amplitude of the respirations. With a blood flow rate of 300 ml/min the patient may lose 600 ml of blood within two minutes after needle disconnection. This will quickly result in a state of shock with increased respiratory frequency and possibly shallower respiration. As soon as the analysis unit 14 has detected e.g. an increased respiratory frequency (>20 respirations/min) for a defined period of time (e.g. 30 sec), the blood pump is stopped and the alarm is triggered.

The alarm might also be triggered via a limit value frame which the analysis unit 14 automatically establishes after the start of blood flow and a waiting period. Around said starting value (e.g. 16 respirations/min) then upper and lower limit values would be defined (for example upper limit value=20 respirations/min=start value+4 respirations/min and lower limit value=12 respirations/min=start value−4 respirations/min).

The invention claimed is:

1. A method for extracorporeal blood treatment, the method comprising:
monitoring, with a radar sensor in an apparatus for extracorporeal blood treatment, a plurality of patients simultaneously who are being treated by the apparatus for extracorporeal blood treatment.

2. The method according to claim 1, the method further comprising:
detecting at least one of respiratory frequency or respiratory amplitude of each of the plurality of patients with the apparatus and an evaluation unit for signals of the radar sensor.

3. The method according to claim 1, further comprising at least one of the steps of:
positioning the radar sensor on the apparatus; and
readjusting the radar sensor by means of a drive for readjusting alignment of the radar sensor relative to the plurality of patients.

4. The method according to claim 1, the method further comprising:
shutting off, with at least one shutoff member of the apparatus, at least one of a line connected to a venous branch or a line connected to an arterial branch.

5. The method according to claim 1, wherein the extracorporeal blood treatment is a dialysis treatment.

6. The method according to claim 1, further comprising:
establishing, with a control unit of the apparatus, a respiratory frequency of each of the plurality of patients by way of signals of the radar sensor.

7. The method according to claim 6, further comprising:
triggering an alarm signal, with the control unit, if the respiratory frequency of any one of the plurality of patients deviates from one or more preset limit values.

8. A method for extracorporeal blood treatment, the method comprising:
monitoring, with a radar sensor in an apparatus for extracorporeal blood treatment, a patient located on a place of treatment by the apparatus for extracorporeal blood treatment;
detecting at least one of respiratory frequency or respiratory amplitude of the patient with the apparatus and an evaluation unit for signals of the radar sensor; and
performing, with the evaluation unit, one or more of the following cycles:
localizing or detecting one or more patients,
converting a detected thorax movement to at least one of respiratory frequency or amplitude,
comparing detected respiratory frequency or amplitude values to at least one predefined limit value,
stopping a blood pump of the apparatus and closing at least one tube shutoff clamp upon at least one of exceeding or falling below the at least one predefined limit value, or
triggering an alarm if the at least one predefined limit value is not observed.

9. The method according to claim 8, wherein the localizing or detecting one or more patients comprises:
at least one of detecting, recognizing, or monitoring movements of a thorax of each patient.

10. The method according to claim 8, wherein the at least one predefined limit value includes a value of 12 to 18 respirations/minute, more than 20 respirations/minute (tachypnea), or less than 10 respirations/minute (bradypnea).

* * * * *